US000001905H

United States Statutory Invention Registration [19]

[11] Reg. Number: H1,905

Hill

[45] Published: Oct. 3, 2000

[54] MECHANISM FOR ADJUSTING THE EXPOSED SURFACE AREA AND POSITION OF AN ELECTRODE ALONG A LEAD BODY

[75] Inventor: Michael R. S. Hill, Minneapolis, Minn.

[73] Assignee: Medtronic, Inc., Minneapolis, Minn.

[21] Appl. No.: 08/821,899

[22] Filed: Mar. 21, 1997

[51] Int. Cl.[7] ..... A61N 1/00

[52] U.S. Cl. ..... 607/122

[58] Field of Search ..... 607/2, 4, 5, 116, 607/119, 121–128; 600/373, 374, 375, 377, 381; 606/47

[56] References Cited

U.S. PATENT DOCUMENTS

| | | | |
|---|---|---|---|
| 3,865,118 | 2/1975 | Bures . | |
| 3,902,501 | 9/1975 | Citron et al. . | |
| 3,903,897 | 9/1975 | Woollons et al. . | |
| 3,949,757 | 4/1976 | Sabel . | |
| 4,289,144 | 9/1981 | Gilman . | |
| 4,365,639 | 12/1982 | Goldreyer . | |
| 4,393,883 | 7/1983 | Smyth et al. . | |
| 4,479,500 | 10/1984 | Smits . | |
| 4,735,205 | 4/1988 | Chachques et al. . | |
| 4,932,407 | 6/1990 | Williams . | |
| 4,944,088 | 7/1990 | Doan et al. . | |
| 4,962,767 | 10/1990 | Brownlee . | |
| 5,056,532 | 10/1991 | Hull et al. | 607/122 |
| 5,403,356 | 4/1995 | Hill et al. . | |
| 5,509,411 | 4/1996 | Littmann et al. | 600/381 |
| 5,578,067 | 11/1996 | Ekwall et al. | 607/122 |

*Primary Examiner*—Charles Jordan
*Assistant Examiner*—Meena Chelliah
*Attorney, Agent, or Firm*—Reed A. Duthler; Harold R. Patton

[57] ABSTRACT

An endocardial pacing and/or cardioversion/defibrillation lead having a plurality of electrodes and a mechanism for adjusting the exposed surface area of one or more electrode and/or the position and/or angular orientation of an electrode along a lead body. A fixed exposed, flexible, elongated commutator surface is provided extending along the lead body intermediate the proximal and distal lead body ends coupled by an electrical lead conductor extending to the proximal end of the lead body. A movable electrode assembly is provided that fits over and slides along the lead body, including the fixed commutator surface, that supports an exposed movable electrode on it. The movable electrode assembly includes at least one flexible, elongated, movable commutator surface within it that is electrically connected with the movable electrode. Electrical contact is established between the movable electrode and the lead connector end through contact of the fixed and movable commutator surfaces in a contact segment of contact area that varies with the relative movement of the movable contact surface with respect to the fixed contact surface. The position and exposed surface area of the movable electrode may be adjusted even further by use of a further electrode adjustable area outer insulating sheath positioned over the movable electrode assembly.

27 Claims, 9 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

MECHANISM FOR ADJUSTING THE EXPOSED SURFACE AREA AND POSITION OF AN ELECTRODE ALONG A LEAD BODY

FIELD OF THE INVENTION

The present invention pertains to improvements in intracardiac electrical stimulation and/or sensing leads, and particularly to endocardial pacing and/or cardioversion/defibrillation leads having a plurality of electrodes and a mechanism for adjusting the exposed surface area and/or position of one or more electrode along the lead body to orient it to a desired anatomical site for sensing and/or stimulation.

DESCRIPTION OF THE BACKGROUND ART

Early cardiac pacemakers provided unipolar or bipolar sensing and pacing of a single chamber of the heart, typically the right ventricle, utilizing a pace/sense lead bearing a single electrode or a pair of electrodes, respectively, in contact with the heart chamber. More recently, pacing and/or sensing of both the atria and the ventricles using a pair of pace/sense leads and/or electrodes (unipolar or bipolar) has become common. These techniques typically provide pacing and/or sensing in the right ventricle, using a right ventricular electrode or electrode pair, and the right atrium, using a right atrial electrode or electrode pair, and generally use separate atrial and ventricular pacing leads to locate the electrodes in the respective chambers. This approach is relatively convenient in both epicardial and endocardial approaches, unless there is difficulty in passing two endocardial leads transvenously through the same blood vessels. In addition, it is sometimes difficult to position the atrial electrode(s) in good electrical contact with the atrial heart tissue.

Atrial and ventricular pacing leads typically employ active or passive, distal end fixation mechanisms, which may or may not constitute a distal electrode, to maintain contact of the distal electrode with endocardial or myocardial tissue to ensure adequate stimulation or sensing. For example, such fixation mechanisms include active, retractable/extendable helical coils adapted to be extended and screwed into the myocardium at the desired site and passive, soft pliant tines (of the type described in commonly assigned U.S. Pat. No. 3,901,502 to Citron) which engage in interstices in the trabecular structure to urge a distal tip electrode into contact with the endocardium. The atrial pacing lead may be formed with a J-shaped bend that allows the atrial electrode to be positioned in the atrial appendage and fixed there through use of the fixation mechanism.

Such pace/sense electrodes and distal tip fixation mechanisms are also currently used in conjunction with large surface area cardioversion/defibrillation electrodes extending proximally along the length of the lead sheath for either right atrial or ventricular placement. Separate electrical conductors and connectors are employed to connect the atrial cardioversion/defibrillation electrodes with an implantable pulse generator (IPG) connector terminal for applying cardioversion/defibrillation shock energy to the respective heart chamber.

In these cases, the inter-electrode separation along the lead body and the effective sizes of the electrodes are fixed and not variable in use. In a somewhat related field of cardiomyostimulation, however, it is known to employ a muscle stimulation electrode having a variable length so that it may be surgically threaded through a muscle mass of a given size as disclosed in commonly assigned U.S. Pat. No. 4,735,205 to Chachques et al. Such electrodes, however, have no application in endocardial cardiac stimulation or sensing leads.

In order to avoid the difficulties and expense of implanting separate endocardial atrial and ventricular leads of the types described, it has long been desired to provide a single atrial-ventricular (A-V) lead that can be used to position both the atrial and ventricular pace/sense electrode(s) and, if warranted, a cardioversion/defibrillation electrode, in desired locations in the right atrium and ventricle. A number of such "single pass" A-V pacing leads have been designed over the years as described in commonly assigned U.S. Pat. No. 4,479,500 to Smits.

In one early approach, atrial and ventricular sense or pace/sense ring-shaped electrodes are simply arranged along the outer sheath of the lead and separated apart by fixed inter-electrode distances. In these designs, the proximal electrode(s) is expected to be positioned in the atrium when the distal tip electrode is fixed in the right ventricular apex as described, for example, in U.S. Pat. Nos. 3,903,897 to Woollons, 4,365,369 to Goldreyer and 4,962,767 to Brownlee. Such leads are typically intended for use in a system for sensing atrial depolarizations or P-waves and both sensing ventricular depolarizations or R-waves and applying ventricular pacing pulses to the ventricular apex.

Because internal heart anatomy varies among individuals, it is difficult to obtain a suitable location of the atrial electrode(s) in a position where they will either sense atrial depolarizations or stimulate the atria properly. Consequently, a number of single-pass A-V leads have been designed having atrial and ventricular electrodes which are adjustable relative to one another along the length of a composite lead body. Several designs encase both atrial and ventricular conductors in a common outer sheath with either the atrial or the ventricular conductor within its own sheath and slideably mounted within a lumen of the outer sheath, allowing axial adjustment of the relative positions of the electrodes.

For example, an early single pass A-V lead is taught in U.S. Pat. No. 3,865,118 to Bures, wherein a ventricular lead sheath is slideably mounted within a lumen extending the length of the atrial lead sheath and extends out the distal end thereof. Electrodes are attached to the distal portions of the atrial and ventricular lead sheaths, and electrical connectors are attached to the proximal ends of these sheaths. Coaxial, atrial and ventricular, coiled wire conductors extend through the atrial and ventricular sheaths to the electrical connectors at the proximal ends thereof. Adjustment of the ventricular lead and electrode relative to the atrial electrode therefore results in corresponding adjustment of the axial separation of the ventricular connector relative to the atrial connector. This results in a lead connector that is not compatible with IPG connector elements that are in fixed separation from one another, requiring a special adapter or modification of the lead connector end.

Another early single pass atrial ventricular lead is taught by Sabel in U.S. Pat. No. 3,949,757. In this lead, the atrial lead sheath is slideably mounted within a lumen of the ventricular lead sheath. As with the Bures lead, adjustment of the relative positions of the atrial and ventricular electrodes changes the relative positions of the electrical connectors, with the disadvantages discussed above.

More recent single pass A-V leads that overcome some of the problems of the Bures and Sabel leads are disclosed in commonly assigned U.S. Pat. Nos. 4,289,144 to Gilman and 4,393,883 to Smyth et al. In these A-V leads, the ventricular sheath is slideably mounted within an outer atrial lead sheath. A bifurcated connector assembly with two connector sheaths is mounted to the proximal end of the lead body. The atrial electrode is electrically connected by a fixed coiled wire conductor extending the length of the outer atrial lead sheath to one connector sheath. The proximal end of the ventricular lead sheath slideably extends through the lumen of the atrial coiled wire conductor and through a lumen of the other connector sheath. The distal end of the ventricular lead sheath extends through a side opening in the outer atrial lead sheath at a point proximal to an atrial lead sheath extension, which may have a J-shape. After the electrode separation is adjusted to the patient's heart, the protruding ventricular lead sheath and the ventricular conductor within it are trimmed. An electrical connector pin is attached to the remaining proximal end of the conductor, a time consuming procedure. After attachment, further adjustment of the lead is precluded, as the ventricular sheath and conductor are then fixed.

A further problem common to several single pass A-V leads is that of sealing the lead at the exit points of the inner lead sheath from the lumens in the outer atrial lead sheath or the proximal connector sheath. In the Smyth and Gilman leads, where a coiled wire conductor is exposed to the lumen of the outer atrial lead sheath that the ventricular lead sheath extends through, a fluid path from that lumen to the exterior of the lead raises the risk of current leakage.

In the '500 patent, the Smits lead is provided with an outer lead sheath having an adjustment means for altering the length of the sheath, such as a circumferentially pleated sheath segment or slideably overlapping sheath segments. A first conductor mounted within the outer lead sheath has means for allowing variation of its length, such as a large diameter coiled segment having increased axial flexibility. The outer sheath is slideably mounted around the inner sheath with the inner sheath protruding therefrom. The inner lead sheath is fixed relative to the proximal end of the outer lead sheath so that variation in the length of the outer lead sheath alters the relationship of electrodes attached to the distal ends of the inner and outer lead sheaths. A connector assembly is attached to the proximal end of the outer lead sheath. The outer sheath may be fixed relative to the inner sheath by engageable projections and indentations on the inner and outer sheaths or by a suture. The Smits lead offers a number of advantages as stated in the '500 patent, but the advantages are offset by a complex manufacture of the lead body.

These prior art references are primarily directed to attaining a single pass A-V lead wherein at least sensing of P-waves is assured by proper location of the atrial sense electrode(s) in the atrium when the ventricular lead distal end pace/sense electrode is lodged in the right ventricular apex. In the field of implantable cardioversion/ defibrillation systems, a number of endocardial leads have been proposed or developed for providing atrial or ventricular cardioversion/defibrillation shocks along with sensing of atrial electrical signals as shown, for example, in commonly assigned U.S. Pat. Nos. 4,932,407 to Williams. The Williams leads include a coronary sinus (CS) cardioversion/ defibrillation lead having an elongated cardioversion/ defibrillation electrode that is intended to be placed into the ostium leading into the CS and blood vessels branching therefrom and more proximally located atrial pace/sense electrode(s) intended to be remain in or near the right atrium for sensing P-waves. The inter-electrode separation between the cardioversion/defibrillation electrode and the atrial pace/ sense electrodes is fixed.

In a somewhat related area, interest has existed for many years in achieving electrode positioning for electrical stimulation of specific surfaces of the right atrium or atrial vessel openings adjacent to autonomic nerves or adjacent specific regions of current pathways for a variety of reasons. For example, research has shown that it may be desirable to stimulate parasympathetic nerves in the sino-atrial (S-A) region of the right atrium that influence the atrial heart rate. In commonly assigned U.S. Pat. No. 5,403,356 to Hill et al. (incorporated herein by reference), the stimulation of the triangle of Koch and/or an area of prolonged effective refractory period elsewhere in the atrium for prevention of atrial tachyarrhythmias is also disclosed. By electrophysiological mapping techniques, it is possible to locate optimum sites for electrical stimulation of the atrium. However, it is difficult to place proximal electrodes of permanent endocardial atrial or ventricular or CS leads of the types described above, having fixed inter-electrode spacing, in proximity to these sites due to variations in their locations, the sizes of the heart chambers, the extent to which the cardioversion/defibrillation electrode is extended into the CS, etc.

In all of these cases, it remains desirable to provide at least one relatively movable electrode for achieving a variable inter-electrode separation from a fixed pace/sense electrode (s) or attachment site so that the movable electrode may be placed optimally and be stabilized in the optimal position while avoiding the problems attendant with connection the proximal end of the lead to the IPG connector terminals. It would also be desirable to have the ability to select the exposed surface area of the electrode to enhance sensing characteristics or optimize stimulation energy distribution.

SUMMARY OF THE INVENTION

It is therefore a primary object of the present invention to provide a simple and flexible implantable endocardial lead providing variable positioning of at least one electrode along the distal segment of the lead sheath.

It is a further object of the present invention to provide a simple and flexible implantable endocardial lead providing variable separation between a least two spaced apart electrodes along the lead sheath.

It is yet a further object of the present invention to provide for variable electrode surface area of the variably positionable electrode.

These and other objects of the invention are realized in an elongated implantable lead of any of the types described above wherein a fixed exposed, flexible, elongated commutator surface is provided extending along the lead body intermediate the proximal and distal lead body ends coupled by an electrical lead conductor extending to the proximal end of the lead body. A movable electrode assembly is provided that fits over and slides along the lead body, including the predetermined segment, that supports an exposed movable electrode on it. The movable electrode assembly includes at least one flexible, elongated, movable commutator surface within it that is electrically connected with the movable electrode. Electrical contact is established between the movable electrode and the lead connector end through contact of the fixed and movable commutator surfaces in a contact segment of contact area that varies with the relative movement of the movable contact surface with respect to the fixed contact surface.

The fixed commutator surface is located at a nominal distance from the distal end of the lead body and a minimum contact segment between the fixed and movable commutator surfaces is defined to maintain an adequate electrical connection. A range of movement of the movable electrode assembly, and the movable electrode, between a maximum or proximal distance and a minimum or distal distance is thereby defined by the relative lengths of the fixed and movable commutator surfaces and the minimum contact segment.

Preferably, the lead body is tubular, the fixed commutator surface is formed of a length of coiled wire wound about the tubular lead body, and the movable commutator surface is formed of conductor wire wound into a coil inside the tubular shaped movable electrode assembly so that the overlapping fixed and movable commutator surfaces are flexible and do not unduly stiffen the lead body. The exposed movable electrode is also preferably formed of a length of coiled wire and may constitute part of the coiled wire forming the movable commutator surface. The movable commutator surface may extend proximally and/or distally of the exposed movable electrode. The coiled wire winding diameter of the exposed movable electrode may be greater than the coiled wire winding diameter of the movable commutator surface(s), or the diameters may be the same.

Insulating sheaths formed as part of the movable electrode assembly extend proximally and distally from the exposed movable electrode and movable commutator surface(s) sufficiently to cover and electrically insulate all of the fixed commutator surface at the extreme proximal and distal positions of the movable electrode.

In a second aspect of the invention, the position of the exposed movable electrode may be adjusted even further by use of a further electrode adjustable area sheath positioned over the movable electrode assembly. The exposed surface area of the movable electrode is also varied by use of the adjustable area sheath. In this case, the exposed movable electrode may be elongated since the final exposed electrode position and surface area is determined by the further electrode adjustable area sheath.

The adjustable sheath may be a solid tubular sheath of a predetermined length exceeding the length of the exposed movable electrode, in which case a proximal or distal end band thereof may be selected as the exposed electrode surface area by relative distal or proximal, respectively, adjustment of the adjustable sheath. Alternatively, the adjustable sheath may have one or more window formed therein so that the window(s) may be selectively positioned along the length and around the circumference of the exposed movable electrode surface. In this case, the exposed electrode surface may be oriented to a desired location or to direct stimulation current in a particular direction to stimulate one of the sites identified herein.

The movable electrode of the present invention may be implemented into a wide variety of leads including the intracardiac leads described above, to allow for positioning of the movable electrode in a desired location for sensing nerve and cardiac electrical signals and for delivering electrical stimulation at a precise location for stimulating nerves or heart tissue. A conventional lead connector end may be employed, and the movable electrode assembly does not unduly increase the outer diameter of the lead body or complicate the implantation procedure.

Advantageously, the movable electrode may be positioned along the lead body to a specific site while taking variations in individual anatomy into account. The movable electrode may be selected in surface area, distance along the length of the lead body and, in certain embodiments, angular orientation for stimulating cardiac tissue or nerves or sensing nerve or cardiac electrical signals for pacing, sensing, cardioversion/defibrillation or nerve stimulation applications. The adjustment of the surface area of the exposed movable electrode in accordance with the second aspect allows for control of electrical stimulation current density at the desired location.

BRIEF DESCRIPTION OF THE DRAWINGS

These and other objects, advantages, and features of the present invention will become evident from the following detailed description of exemplary preferred embodiments thereof in view of the following drawings wherein the same or like components are identified by the same drawing numbers or indicia, and wherein.

DETAILED DESCRIPTION OF THE PREFERRED EMBODIMENTS

The present invention is described in a number of preferred embodiments having a number of intended uses as set forth in the preceding description, and other uses will become apparent to those of skill in the art. In the preferred embodiments, a single variable position electrode is described that may be positioned within a range of possible locations along a segment of the length of an endocardial lead outer sheath in relation to the distal end thereof. It will be understood that the lead may include at least one further variable position electrode so that the inter-electrode spacing and location of the electrodes along the lead sheath may be optimized for a particular application. In certain applications, the distal end of the lead sheath may include a pace/sense electrode(s) or an elongated cardioversion/defibrillation electrode and/or a fixation mechanism for stabilizing the lead.

The embodiments of the present invention are further described as having coaxial lead conductors employing proximal, variable position, ring-shaped electrodes and in-line connector assemblies and provided with an innermost lumen for receiving a stiffening stylet as is conventional and widely employed in the art. It will be understood that the lead conductor configuration may alternatively take any of the known forms, including separate, single or multi-filar coiled wire or straight conductors located in separate lead body lumens or multi-filar, separately insulated, parallel wound, coiled wire conductors of the type described in commonly assigned U.S. Pat. No. 4,944,088 to Doan et al. and in Canadian Pat. No. 1,146,228 to Upton, incorporated herein by reference in their entireties. Finally, the present invention is described in its preferred embodiments as having unipolar or bipolar atrial and ventricular electrodes. However, configurations employing multi-polar electrodes are within the intended scope of the invention. A wide variety of configurations employing different combinations of these elements are within the intended scope of the invention.

Figure 1:
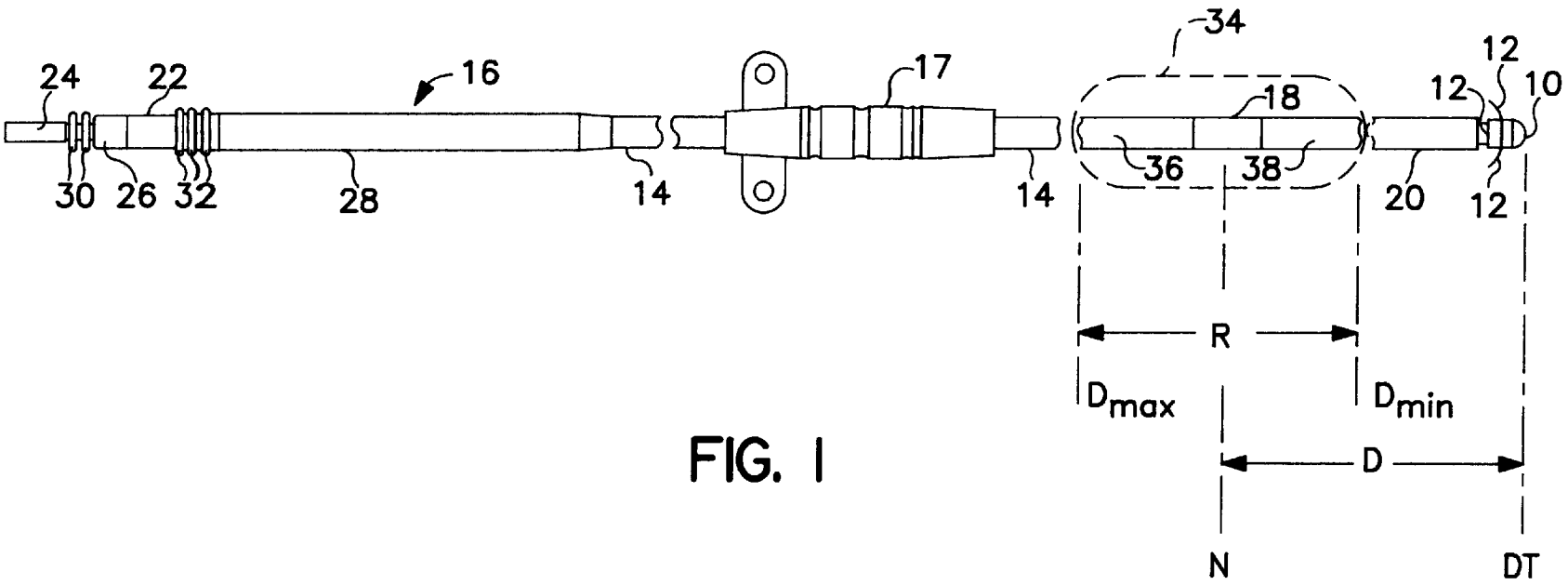
FIG. 1 is a plan view of an endocardial lead incorporating the present invention in which a variable position electrode assembly and variable area sheath are employed to define a location and size of an electrode proximal to the distal end of the lead.

In FIG. 1, a plan view of a generic, single pass, lead embodying the first aspect of the present invention is depicted. In this embodiment, it will be assumed for convenience of illustration and description that the lead body is formed using co-axial coiled wire lead fabrication techniques that are well known in the art having an inner lumen for receiving an inner, coiled wire, lead conductor and at least one outer, co-axial lumen surrounding the inner lumen for receiving an outer elongated, coiled wire, lead conductor. A pace/sense electrode 10 and a pliant tine, passive fixation mechanism 12, for example, are located at the distal end of a distal extension of an inner lead sheath 20 that extends from a fixed commutator surface (described below) forming part of the lead body at the distal terminus of an elongated, outer lead sheath 14 and encased by a variable position, movable electrode assembly 34. The elongated outer insulating lead sheath 14 extends from a proximal, in-line, connector assembly 16 to the fixed commutator surface. The inner lead sheath 20 extends from the fixed commutator surface of the movable electrode assembly 34 to distal pace/sense electrode 10. A suture sheath 17 is mounted around insulating sheath 14 to be moved along it and fixed at a desired location to anchor the outer lead sheath 14 at the point of venous entry in a manner well known in the art. Connector assembly 16 includes a connector pin 24 and a ring-shaped connector element 22, separated by an insulating sheath 26. and a distally extending reinforcing sheath 28. The connector assembly 16 is provided with resilient sealing rings 30 and 32, which seal the connector assembly 16 when it is inserted into an elongated receptacle in a connector block mounted to an IPG (not shown).

In accordance with a first aspect of the present invention, the variable position electrode assembly 34 supports an exposed ring-shaped, or partial ring-shaped segment, movable electrode 18. The movable electrode 18 is supported between proximal and distal movable insulating sheaths 36 and 38 of the assembly 34 adapted to be positioned over the fixed commutator surface of the lead body and the exterior surface of outer and inner lead sheaths 14 and 20, respectively. The variable position electrode assembly 34 also includes an inner commutator surface that contacts the exterior commutator surface of lead sheath 14 in a selectable area of contact as described in detail with reference to FIGS. 2–9. In accordance with a second aspect of the invention, the exposed surface area of movable electrode 18 may preferably be adjusted through the use of a further outer insulating electrode area sheath as described below in reference to FIGS. 7–9.

The connector pin 24 is electrically and mechanically connected to the distal tip electrode 10 by an elongated inner coiled wire electrical conductor (or a conductor of one of the other conductor types listed above) extending within the inner lead sheath 20 for the full length of the lead. Similarly, the connector ring element 22 is electrically and mechanically connected by an elongated outer coiled wire conductor (or one of the other conductor types listed above) located within outer sheath 14 which is electrically connected to the movable electrode 18 through the commutator mechanism described in reference to FIGS. 2–6.

Connector pin 24, ring member 22, variable electrode 18, and distal tip electrode 10 are preferably fabricated using inert conductive metals such as platinum, Elgiloy® alloy, MP35N or stainless steel. Insulating sheaths 26 and 28 are preferably fabricated of silicone rubber, and outer insulating sheath 14, inner insulating sheath 20 and movable proximal and distal, movable insulating sheaths 36 and 38 are preferably fabricated of polyurethane or silicone rubber.

In FIG. 1, the distal tip of the lead constitutes a reference point DT with respect to a range R of possible locations of the ring electrode 18 along outer lead sheath 14 about a nominal location N and between minimum and maximum distances $D_{min}$ and $D_{max}$. The range R and the distance D from the distal tip DT to the nominal position N may be selected for the particular applications depicted in FIGS. 10–15 and other applications that may become known to those of skill in the art.

Figure 2:
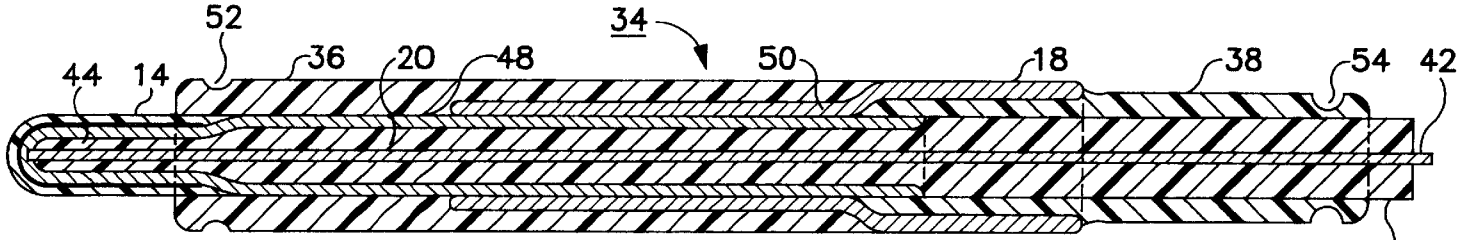
FIGS. 2–4 are each a side cross-section view of a first variation of the construction of a variable position electrode assembly of FIG. 1 and depicting a range of movable electrode locations.

FIG. 2 shows a side sectional view of a first embodiment of the movable electrode assembly 34 without an outer sheath for adjusting the exposed surface area of the movable electrode 18. For simplicity of illustration, the lead body 40 is shown as solid having a straight inner conductor 42 extending between the distal tip electrode 10 and the proximal connector pin 24 (which may constitute one manner of constructing the lead body 40). It will be understood that the inner conductor 42 may be a coiled wire conductor coiled to define an inner lumen for receiving a stiffening stylet, as is conventional in the art. Similarly, the outer conductor 44 is depicted as a solid, whereas in practice, it is preferably constructed as a coiled wire conductor that may co-axially surround the inner conductor 42 and be insulated therefrom by the inner lead sheath 20 extending distally to the connector assembly 16 in a manner well known in the art. Other conductor types of the types listed above may be alternatively employed to perform the functions of the inner and outer conductors 42 and 44.

The movable electrode assembly 34 further preferably comprises a flexible commutator mechanism including an elongated, fixed commutator surface 48 electrically connected to the distal end of the outer conductor 44. The fixed commutator surface 48 is exposed at the terminus of outer lead sheath 14 so that it may make electrical contact with an elongated movable commutator surface 50 within the proximally extending, movable insulating sheath 36 in an overlapping, band-shaped, contact segment. Preferably, the fixed commutator surface 48 is formed of an elongated coiled wire conductor that is closely wound over an enlarged diameter section of the inner lead sheath 20 (or a flexible spacer sheath over inner lead sheath 20). Alternatively, the winding may be spaced so that the coil turns are partially embedded in inner lead sheath 20 (or such a flexible sheath) leaving at least the outermost portion of the coils exposed in a manner known in the art for the fabrication of exposed, coil wire turn electrodes.

In the preferred embodiment wherein the outer conductor 44 is formed of a single or multi-filar coiled wire conductor, the fixed commutator surface 48 may be formed of a number of turns of the coiled wire outer conductor 44 at the distal end thereof that are expanded in diameter to approximate that of the outer lead sheath 14. Where the outer conductor 44 is formed of a straight wire or in another manner, it may be electrically and mechanically connected to the coiled wire conductor of the fixed commutator surface 48 by welding or the like in a manner well known in the art.

Similarly, the movable commutator surface 50 is preferably formed of a length of coiled wire conductor having closely wound turns or space wound turns insulated by or partially embedded within the proximally extending, movable insulating sheath 36. The movable electrode 18 is preferably formed of a number of turns of the same coiled wire conductor extending proximally or distally from the coiled wire turns forming the movable commutator surface 50 that are expanded in diameter to fit over distal insulating sheath 38. Again, the movable electrode 18 may be formed of closely wound or space wound turns of the coiled wire conductor in a manner well known in the art. Alternatively, the movable electrode 18 is formed of a solid conductive ring that is electrically and mechanically connected to the movable commutator surface 50 through crimping and welding techniques well known in the art. In that case, the conductive ring movable electrode 18 may be attached directly over turns of the movable commutator surface 50, rather than offset distally or proximally as shown.

For convenience of illustration, the coiled wire turns of the fixed commutator surface 48 are depicted as a conductive tubular element. It will be understood that the fixed and movable commutator surfaces 48 and 50 are preferably both formed of coiled wire turns so that the lead body 40 remains flexible over their lengths. The coiled wires turns forming the fixed and movable commutator surfaces may be partially embedded in insulation sheathes. As a result of using coiled wire conductors, the lead body 40 may bend in the region of the movable electrode assembly 34 and make intimate contact with the endocardial wall or a cardiac vessel wall in a desired location and is not subjected to stresses that would arise if it were not flexible in that region.

Alternatively, the fixed commutator surface 48 may be formed of a length or parallel lengths of straight wire conductor embedded in the outer sheath 20 and electrically connected to the coiled wire outer conductor 44 or to a straight wire outer conductor(s) 44. The movable commutator surface 50 may alternatively take the form of discrete conductive bands or segments bearing against the straight wire conductor, fixed commutator surface 48.

The movable electrode assembly 34 has an inner diameter that snugly fits over the outer diameter of the outer sheath 14, the exposed coil surfaces of the fixed commutator surface 48, and the distal section of the inner lead sheath 20. The inner and outer diameter dimensions are selected to provide good electrical contact between the movable commutator surface 50 and the fixed commutator surface 48 while still allowing relative movement within the range R. The exposed portions of the coiled wires of the fixed and movable commutator surfaces 48 and 50 making sliding and electrical contact with one another in the contact segment may be shaped as spiral bands or as flattened outer or inner turn surfaces to optimize electrical contact and the ability to move the movable electrode assembly 34. A lubricant, e.g. silicone oil, may be used to allow relative movement while providing an interference fit of the inner and outer diameters of the movable and fixed commutator surfaces 50 and 48.

The lengths of the proximally and distally extending, movable insulating sheaths 36 and 38 may vary from those shown in FIG. 2. The lengths are selected to maximize coverage and insulation of the fixed commutator surface 48, other than the contact segment, at extreme proximal and distal positions of the movable electrode assembly 34 within the range R. The range R is defined by the relative lengths of the fixed and movable commutator surfaces 48 and 50. Only limited lengths of each commutator surface 48 and 50 need to overlap in the contact segment to make adequate electrical contact. Because the commutator surfaces 48 and 50 are formed of coiled wire turns, it is likely that electrical contact may be provided at a large number of contact points along the band-shaped contact segment. A large surface area contact segment is not necessary for sensing electrical signals or for low energy stimulation of the heart chamber or autonomic nerves or the like.

However, it is necessary to stabilize the area of the contact segment from relative movement due to the beating action of the heart or patient exercise in order to minimize electrical noise that may result from such relative movement. Consequently, in a first variation as illustrated, proximal and distal suture grooves 52 and 54 are provided to receive sutures to tie down the movable electrode assembly when an optimum distance D is selected for a given location in a given patient. Other suture grooves may be provided along a particularly lengthy movable electrode assembly 34. The sutures stabilize the area of contact to minimize electrical noise, seal the contact surfaces from ingress of body fluids, and otherwise maintain the distance D. In order to electrically insulate and preferably avoid fluid ingress into the junction of the fixed and movable commutator surfaces 48 and 50, at least a proximal section of the inner lead sheath extending from the distal terminus of the fixed commutator surface 48 is preferably enlarged in diameter as depicted or encased in a further sheath providing an outer diameter consistent with that of outer lead sheath 14 and fixed commutator surface 48. For purposes of the present invention, the enlarged diameter section of the inner lead sheath 20 by either method may be considered as a distal extension of the outer lead sheath 14.

As described below in reference to FIG. 9, the proximally extending, movable insulating sheath 36 may extend proximally into proximity with the proximal connector assembly 16 so that the movable electrode 18 it may be adjusted by the physician after the lead 10 is positioned in the heart. In other words, the proximal end of the proximally extending, movable insulating sheath 36 can be grasped to move the elongated sheath proximally or distally with respect to the fixed commutator surface 48.

Figure 3:
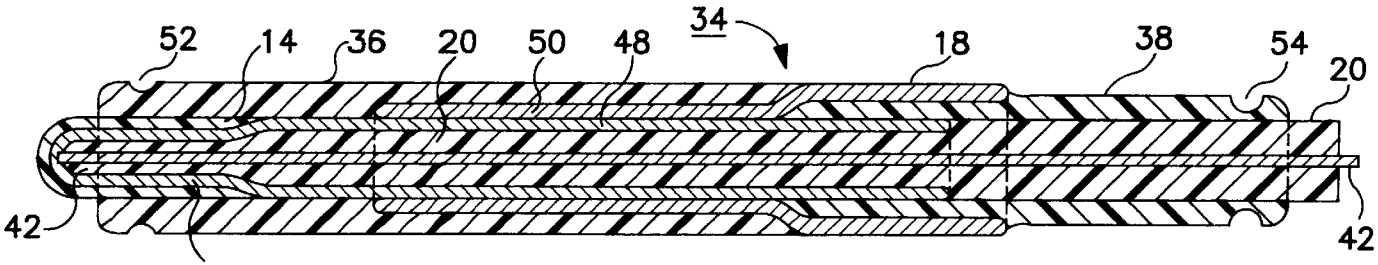
Figure 4:
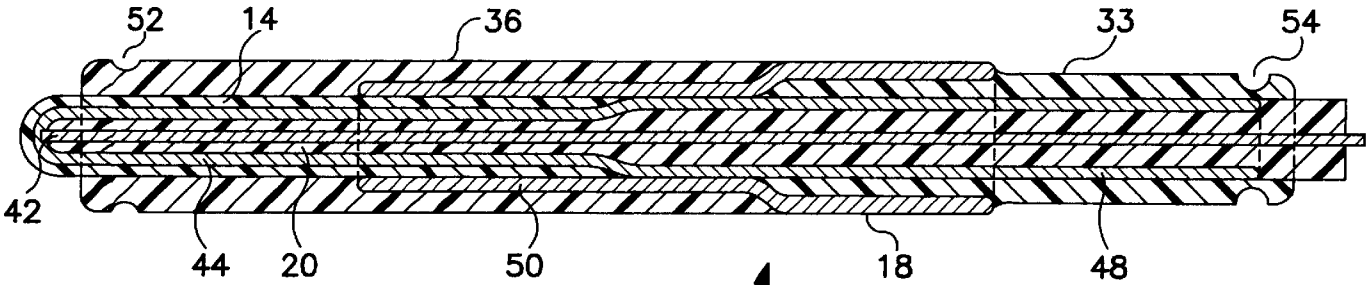

FIGS. 3 and 4 depict other relative displacements of the fixed and movable commutator surfaces 48 and 50 of the movable electrode assembly 34 within its adjustment range R illustrated in FIG. 1. In FIG. 2, the movable electrode 18 is positioned at the distal extreme of the range R or a minimum distance $D_{min}$ (FIG. 1), depending on a safe minimum length of overlap of the fixed and movable commutator surfaces 48 and 50 and the length of the proximally extending, movable insulating sheath 36. In FIG. 4, the movable electrode 18 is positioned at the proximal extreme of the range R or the maximum distance $D_{max}$, (FIG. 1) depending on the safe length of overlap of the fixed and movable commutator surfaces 48 and 50 and the length of the distal movable insulating sheath 38. In FIG. 3, the movable electrode 18 is positioned intermediate the minimum and maximum distances $D_{min}$ and $D_{max}$.

The range R thus depends on the lengths of the fixed and movable commutator surfaces 48 and 50, the lengths of the proximally and distally extending movable insulating sheaths 36 and 38 and the minimum length of overlap of the fixed and movable commutator surfaces 48 and 50. The exterior surfaces of the outer lead sheath 14 and the distal extension of the inner lead sheath 20 may be marked with markers identifying the minimum and maximum distances $D_{min}$ and $D_{max}$. Alternatively, movement of the movable electrode assembly 34 beyond the range R may be physically inhibited by stops formed in the exterior surfaces of the outer lead sheath 14 and the distal extension of the inner lead sheath 20.

Figure 5:
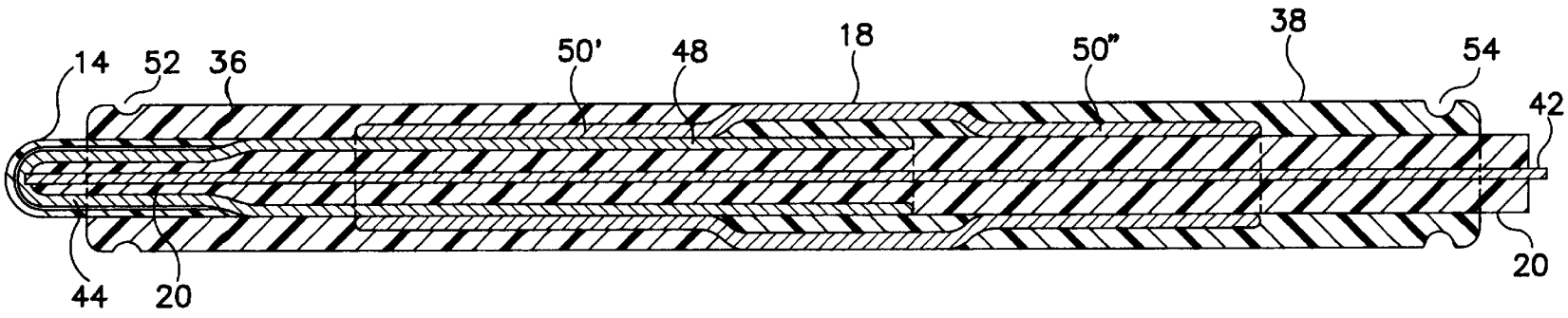
FIGS. 5 and 6 are each a side cross-section view of a second variation of the construction of the variable position electrode assembly of FIG. 1.
Figure 6:
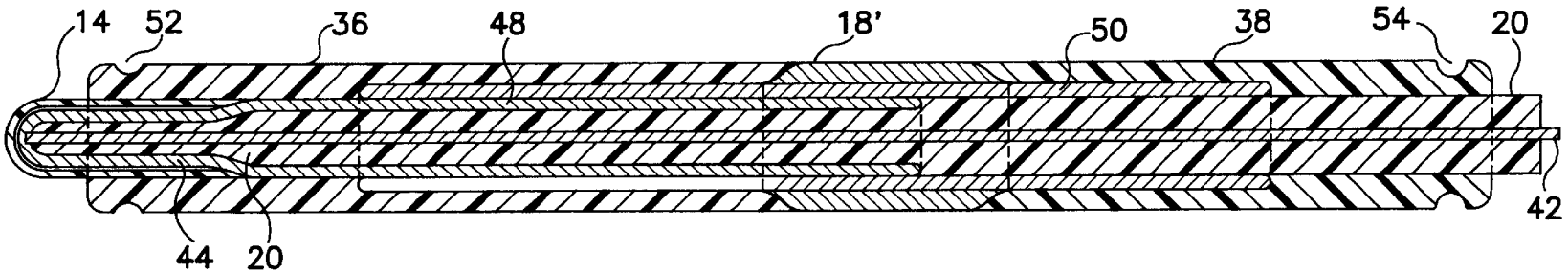

FIG. 5 depicts a variation of the first embodiment wherein the movable electrode 18 is positioned between a proximal and distal movable commutator surface sections 50' and 50". Again, the movable electrode 18 and the proximal and distal movable commutator surface sections 50' and 50" are preferably formed of an extension of the outer lead conductor 42 formed as a coiled wire conductor having differing coil inner diameters to provide the commutator surface 50. This variation may be employed advantageously to provide elongated cardioversion/defibrillation movable electrodes 18. Alternatively, the movable electrode 18 may be formed of a solid metal band 18' that is crimped and attached to the coiled wire, movable commutator surface 50 extending proximally and distally as shown in FIG. 6.

It should also be noted that the exposed electrode 18 may be effected as either a band or ring shape, as depicted, or may be a patch or segment of a band shape to provide the capability of angularly orienting the movable electrode 18 toward a desired anatomical feature as described below. This limited electrode may be effected by the form of the proximally and distally extending, outer insulating sheathes 36 and 38 and/or by the shape of the attached band 18'. It is possible to form the movable electrode 18 as simply an exposed band or segment or patch of the coiled wire conductor forming the movable commutator surface 50 without the expanded diameter of movable electrode 18 as depicted in FIGS. 2–6 and 7–9. In this case, the movable electrode 18 is simply an exposed exterior portion of the movable commutator surface 50 in the region of electrode 18' of FIG. 6, for example. The exposed segment or patch shaped movable electrode 18 may be effected by simply forming the proximally and distally extending, movable insulating sheathes 36 and 38 as a single insulating sheath with a window opening in it to define the angularly orientatable movable electrode 18. A particular angular orientation may be effected by rotation of the movable commutator surface 50 and attached movable electrode 18 over the fixed commutator surface 48.

Figure 7:
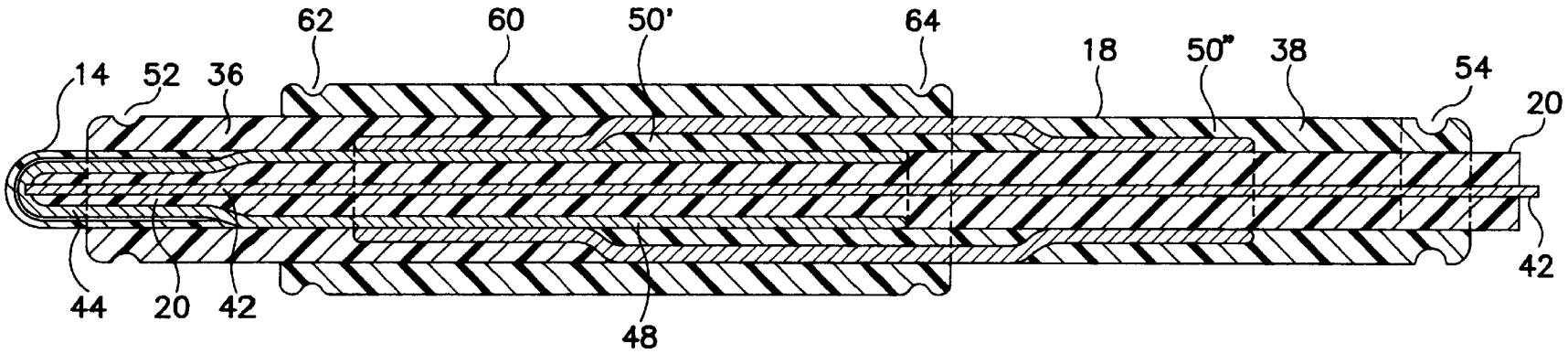
FIGS. 7 and 8 are each a side cross-section view of the variable position electrode assembly of FIG. 1 together with a variable area sheath for adjusting the exposed movable electrode surface area depicted in proximal and distal locations in accordance with a second aspect of the invention.
Figure 8:
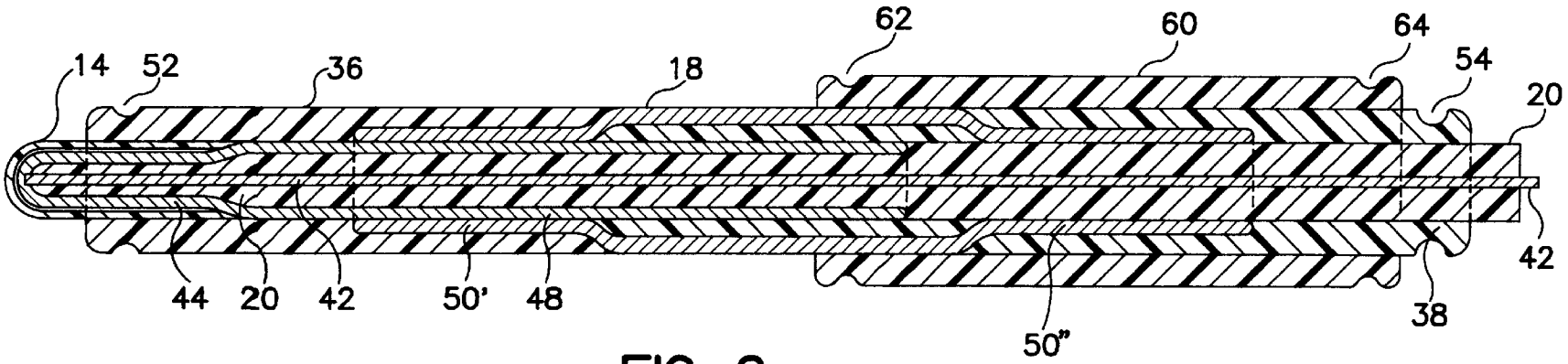

The second embodiment of the invention contemplates the adjustment of the surface area of the movable electrode 18 or 18' with a further movable, tubular, adjustable area, insulating sheath 60 that may be fitted over it and moved distally or proximally with respect to the position of the electrode 18. In this embodiment, the movable, flexible coiled wire, electrode 18 and the associated fixed and movable commutator surfaces 50 may be fairly lengthy to allow for a wide adjustment range R. Then, the adjustment may be further fine tuned by adjusting the location of window opening(s) or ends of the adjustable area insulating sheath 60 and applying sutures to the suture grooves 62 and 64 or otherwise fixing the adjustable area sheath 60 in place. FIG. 7 shows a proximal location of such an adjustable area insulating sheath 60 leaving a distal band-shaped section of the movable electrode 18 exposed. Similarly, FIG. 8 shows a distal location of the adjustable area insulating sheath 60 leaving a proximal band-shaped section of the movable electrode 18 exposed for either sensing cardiac signals or stimulating a particular location in a heart chamber or vessel. The adjustable area insulating sheath 60 may be employed with any of the leads depicted in FIGS. 1–6 and equivalents thereto.

Figure 9:
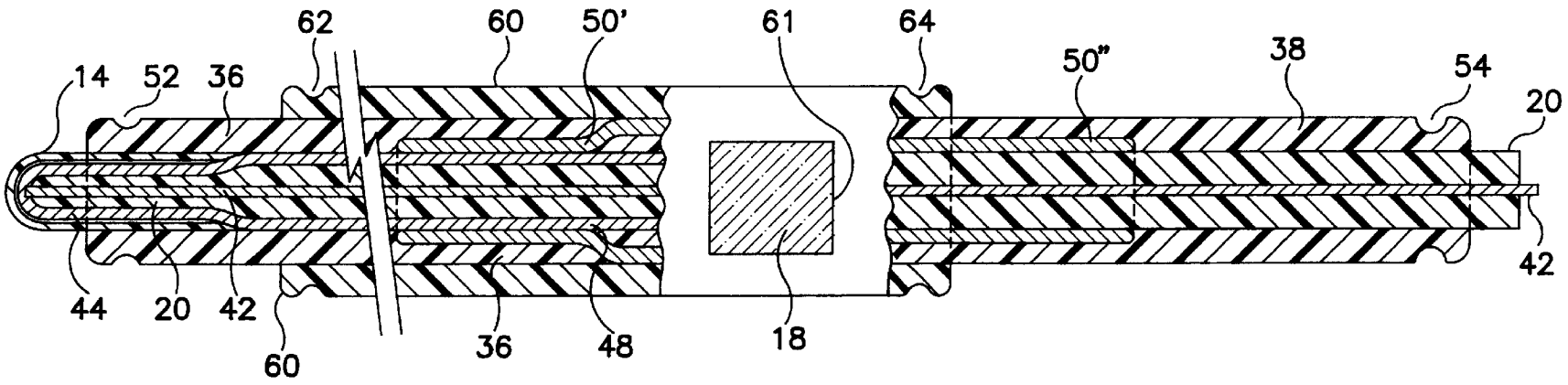
FIG. 9 is a partial cross-section view of the variable position electrode assembly of FIG. 1 together with a variable electrode position and angular orientation determining sheath for locating and orienting a sheath window over the movable electrode surface in accordance with a variation of the second aspect of the invention.

In the variation of this aspect of the invention depicted in FIG. 9, the movable or adjustable area insulating sheath 60 is provided with one or more window opening 61. The adjustable area insulating sheath 60 determines a variable electrode position and angular orientation for locating and orienting the sheath window opening 61 over an electrode surface 18" defined in size by the window opening 61 so that electrical stimulation current flows in a desired direction or sensing of electrical signals is from a desired direction. Although only a single position is depicted, it will be understood that the adjustable area insulating sheath 60 may be positioned along the length of overlap of the commutator surfaces in the manner described above with respect to FIGS. 2–4 or 5 and 6. The adjustable area insulating sheath 60 may also be rotated about the movable electrode assembly to orient the window opening to the desired angle. This variation is particularly useful in orienting the exposed electrode surface in an optimum direction along the length of the lead body within the range R for sensing or stimulating nerves or fat pad areas as described below.

In this aspect of the invention, it should be noted that it may be possible to employ a continuous length of flexible conductor, e.g. a length of coiled wire conductor, as both the commutator surface and the movable electrode surface, wherein the length of coiled wire conductor has a common coil winding diameter. For example, the full length of the movable commutator 50 depicted in the embodiment of FIG. 6 (without the band electrode 18') could be employed as the movable electrode that is positionable to overlap with the elongated fixed commutator 48. Then, the exposed surface area of the movable electrode 18 would be governed by the positioning of the adjustable area insulating sheath 60.

Although a single movable electrode assembly 34 (and optionally adjustable area insulating sheath 60) is described to this point, it will be understood that a fixed ring electrode or a second movable electrode assembly may be provided along the outer lead sheath 14 spaced proximally from the first movable electrode assembly 34 by simply enlarging the lead body to accommodate the additional lead conductor and insulating sheath in separate lumens or by employing the separately insulated conductor wires wound together in the same lumen in the manner disclosed in the above-incorporated '088 patent.

In accordance with a further aspect of the present invention mentioned above and illustrated in FIG. 9, for example, the proximally extending, movable insulating sheath 36 may extend a distance sufficient that it ends adjacent to the proximal connector assembly 16 but spaced from it, exposing the proximal suture groove 52 when the lead is transvenously implanted. The distal suture groove 54 may be eliminated, and the distal end of distally extending, movable insulating sheath 38 may tightly fit over the distal extension of inner lead sheath 20. In this manner, the insulating sheath 36 and the movable electrode assembly 34 may be manually manipulated by the surgeon when the electrodes on the lead are positioned within the heart. In this embodiment, the movable electrode assembly 34 may be adjusted in situ while observing the cardiac structure and the movable electrodes through fluoroscopy or other visualization techniques. The position of the adjustable electrode assembly 34 may also be tested by delivering stimulation pulses and/or monitoring electrical signals of the heart or nerves. After an optimum position is attained, the suture may be tied about the proximal suture groove 52 to hold the desired position.

Similarly, with respect to the second aspect of the invention described above with respect to FIGS. 7–9, the movable, adjustable area, insulating sheath 60 may also extend proximally so that it may be manipulated by the surgeon in the same manner. Markers may be provided on it and on the underlying proximally extending, movable insulating sheath 36 to guide the adjustment of the exposed surface area and/or orientation of the electrode 18.

Exemplary applications for endocardial leads of the type described above having one or more movable electrode assembly 34 with and without the adjustable area sheath 60 area are depicted schematically in FIGS. 10–15. In each case, it will be understood that the ideal implantation location may be visualized using fluoroscopy, since the movable electrode assembly 34 is radiopaque, and that the lead may be withdrawn for adjustment or adjusted manually in situ by manipulation from the proximal lead of the movable electrode 18 if it appears to be too superior or inferior to the desired location. Once a desired general location is confirmed, the adjustable area sheath 60 may be used to fine tune the location and size of the exposed surface of the movable electrode 18.

Figure 10:
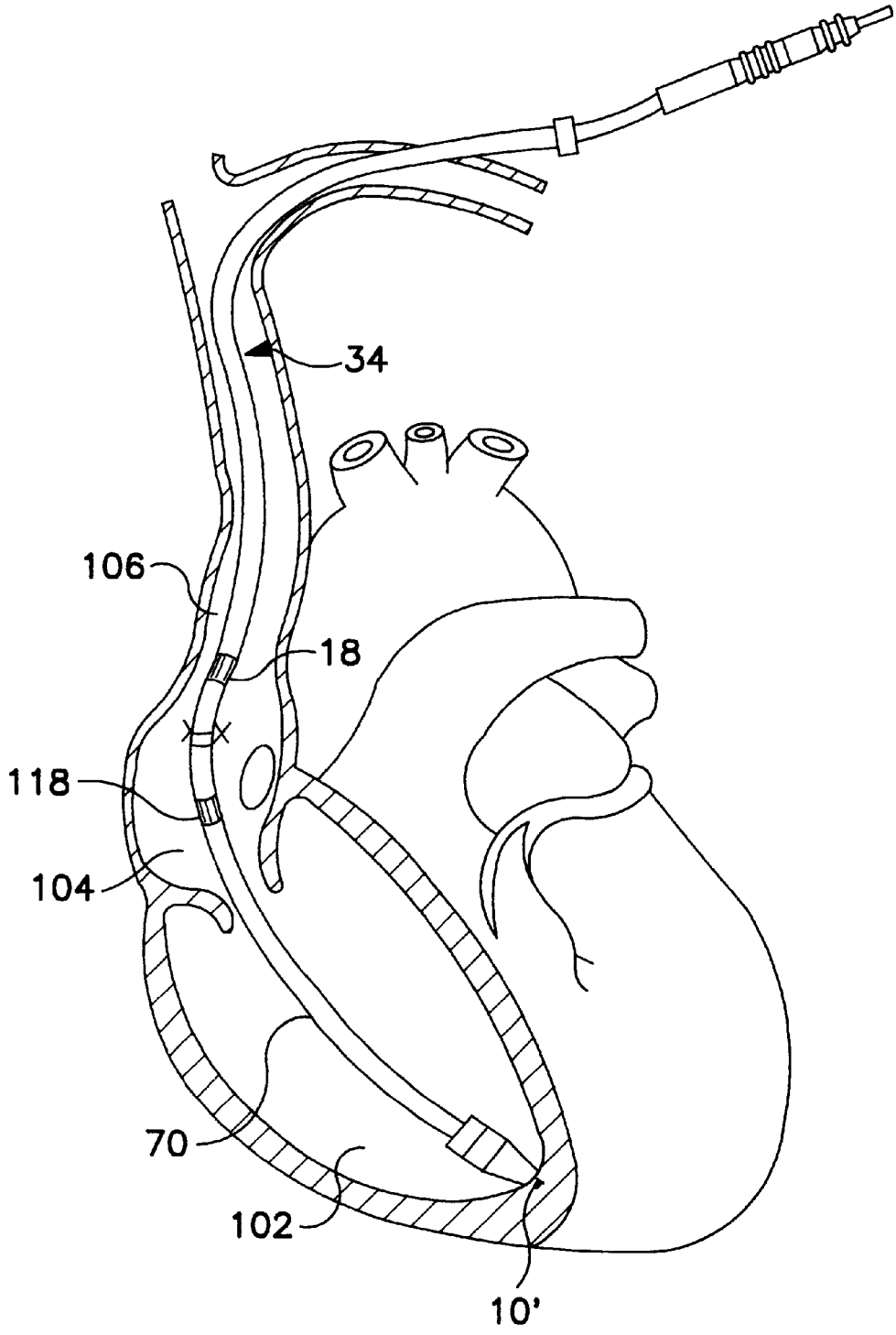
FIG. 10 is a schematic illustration of an application of the present invention in a single pass, endocardial, A-V pacing lead positioned in the heart wherein the movable electrode assembly may be positioned in the atrium or superior vena cava (SVC) for sensing or stimulating nerves or atrial heart tissue.

In FIG. 10, a single pass, A-V lead 70 is depicted having the form shown in FIG. 1 and one of the movable electrode configurations depicted in FIGS. 2–9 in relation to the heart 100. The lead 70 is shown with a screw-in fixation electrode 10' holding the distal tip in the apex of the right ventricle 102. The distance D that the movable electrode 18 is adjusted to allows the electrode 18 to be positioned high in the right atrium or the SVC 106 in the location suggested in the '767 patent adjacent to the S-A node to facilitate sensing of the atrial EGM, particularly the P-wave. A second fixed (or adjustable) electrode 118 is also incorporated in the lead 70 of FIG. 10 for bipolar sensing or stimulation, but may be absent for unipolar sensing or stimulation.

Figure 11:
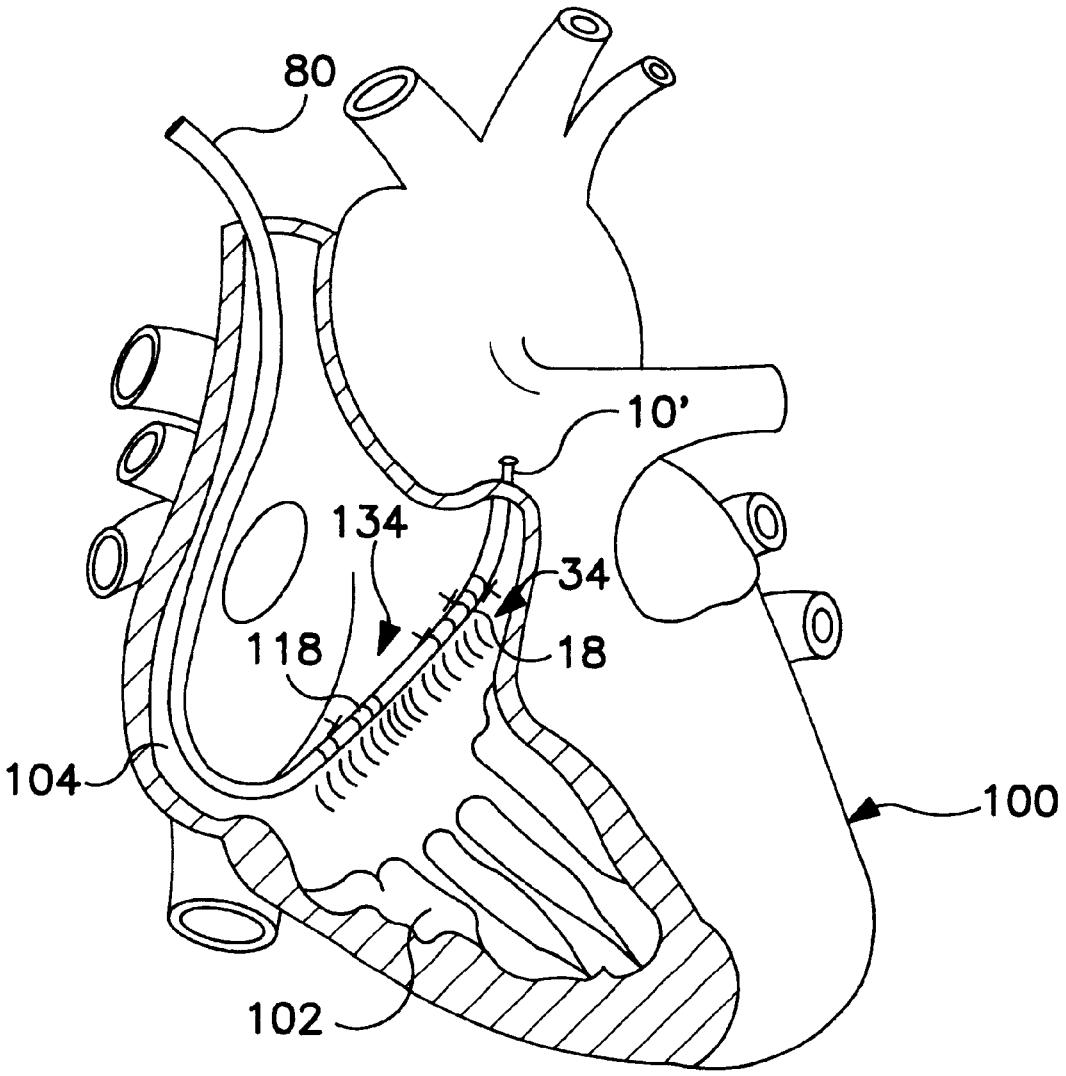
FIG. 11 is a schematic illustration of an application of the present invention in an atrial J-shaped endocardial lead positioned in the heart for effecting either nerve or heart tissue stimulation and sensing at a selected location of the movable electrode assembly with respect to nerves or atrial heart tissue.

FIG. 11 depicts an atrial J-shaped lead 80 also having first and second movable electrode assemblies 34 and 134 positioned along the lead outer sheath in a desired location in the right atrium 104. The position of the movable electrodes 18, 118 may be adjusted to optimize detection of atrial EGM signals emanating from near the S-A node or the fat pads in the triangle of Koch as described in the above-incorporated '356 patent or other areas of the atrial wall or the SVC 106 that the lead outer sheath 14 bears against to detect desired signals or apply electrical stimulation to.

Figure 12:
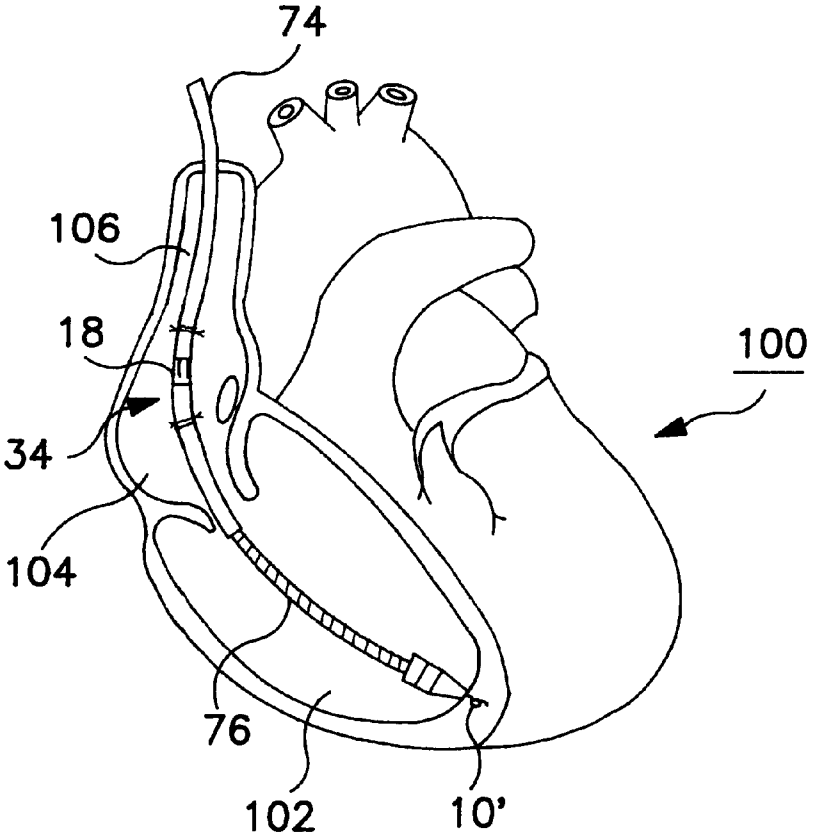
FIG. 12 is a schematic illustration of an application of the present invention in a single pass A-V lead having a movable electrode assembly for locating a sense or stimulation electrode in the right atrium or superior vena cava proximally to a ventricular cardioversion/defibrillation electrode positioned in the right ventricle of the heart.

In a further application, the electrodes 18, 118 in FIGS. 11 and 12 may be positioned to facilitate delivery of electrical stimulation through the atrial wall or the SVC wall to autonomic nerves to influence sinus heart rate, the A-V interval, and blood pressure or the like. For example, vagal nerve stimulation may be effected through the atrial wall by an electrode 18 that is oriented in the manner described above with respect to the variation of FIG. 9 towards the vagal nerves. The vagal stimulation may be delivered during an episode of atrial fibrillation or tachycardia in order to slow the ventricular heart rate response to the atrial heart rate.

Figure 13:
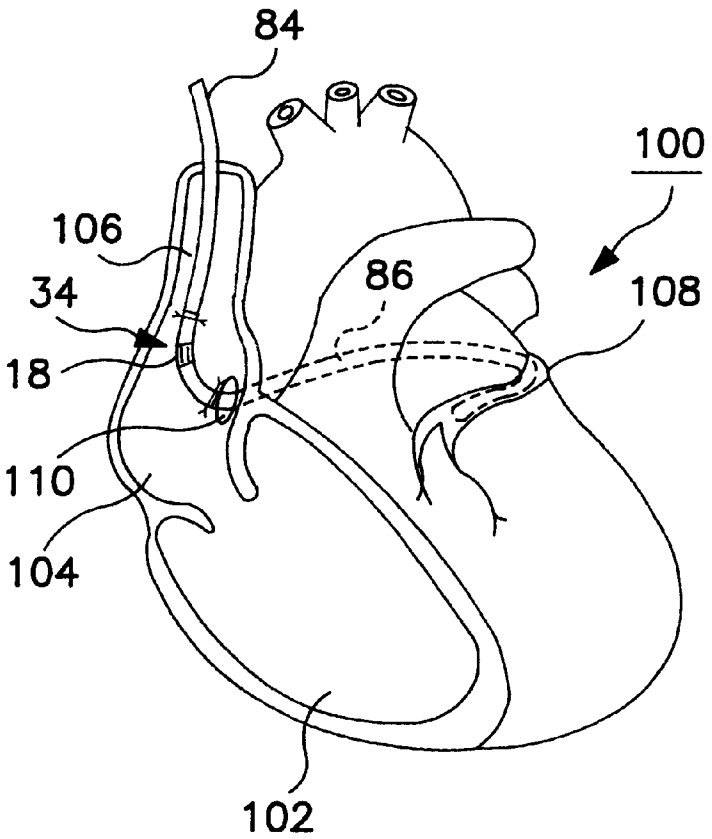
FIG. 13 is a schematic illustration of an application of the present invention in a single pass A-V lead having a movable electrode assembly for locating a sense or stimulation electrode in the right atrium or SVC proximally to an elongated cardioversion/defibrillation electrode positioned in the coronary sinus of the heart.

The present invention may also be used in endocardial leads having elongated cardioversion/defibrillation electrodes extending proximally from the distal tip thereof toward the more proximally located movable electrode(s) 18. FIG. 12 depicts a ventricular cardioversion/defibrillation lead 74 having a cardioversion/defibrillation electrode 76 in such a location and the movable electrode assembly 34, located proximally thereto in the manner of FIG. 10. FIG. 13 depicts a CS lead 84 extending into the ostium opening 110 and having a cardioversion/defibrillation electrode 86 of the type shown in the above-referenced '407 patent located in the CS 108. The proximally located, movable electrode assembly 34 can be adjusted in position to be located outside the ostium opening 110 and in an optimum location for sensing the P-wave and/or pacing the atrium.

Figure 14:
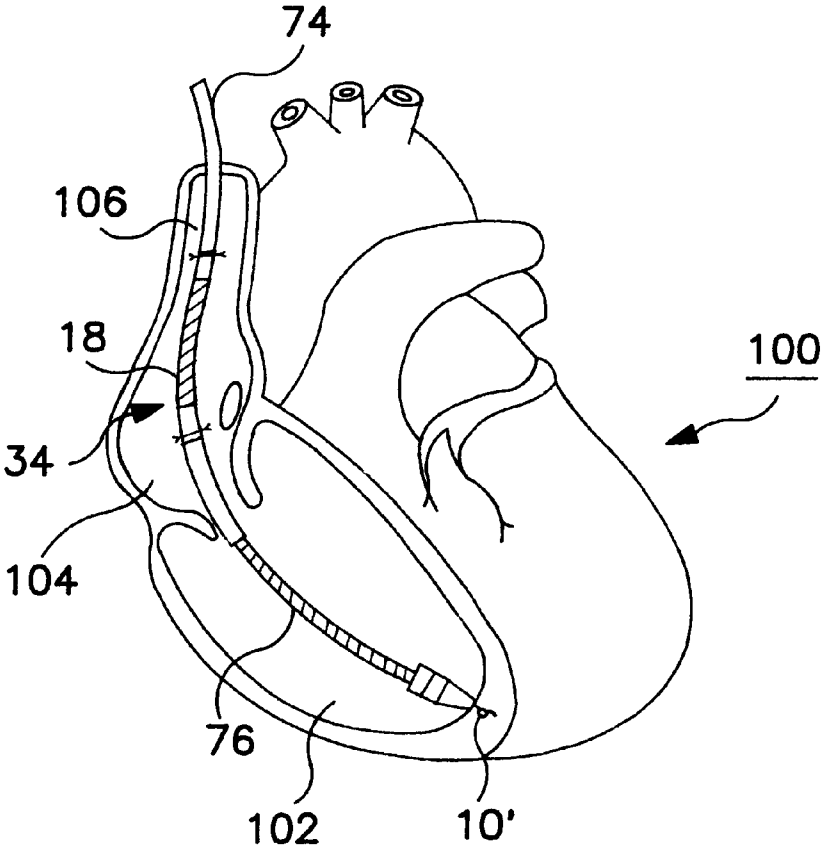
FIG. 14 is a schematic illustration of an application of the present invention in a single pass A-V lead having a movable electrode assembly for locating an elongated cardioversion/defibrillation electrode in the right atrium and/or SVC proximally to a ventricular cardioversion/defibrillation electrode positioned in the right ventricle of the heart.

FIG. 14 is a schematic illustration of an application of the present invention in a single pass, atrial and ventricular cardioversion/defibrillation lead 174 having a ventricular cardioversion/defibrillation electrode 176 located in the right ventricle 102 and a movable cardioversion/defibrillation electrode assembly 34, located proximally thereto in the right atrium 104 and/or SVC 106. In this case, the movable electrode assembly 34 is an elongated coiled wire conductor, exposed movable electrode 18 adjustably located in the right atrium 104 and/or SVC 106 for delivering cardioversion/defibrillation shocks between the atrial and ventricular cardioversion/defibrillation electrodes in a manner well known in the art. For atrial cardioversion/defibrillation alone, the ventricular cardioversion/defibrillation electrode 176 may be eliminated. In both cases, the distal ventricular pace/sense electrode and fixation mechanism 10 may be retained.

Figure 15:
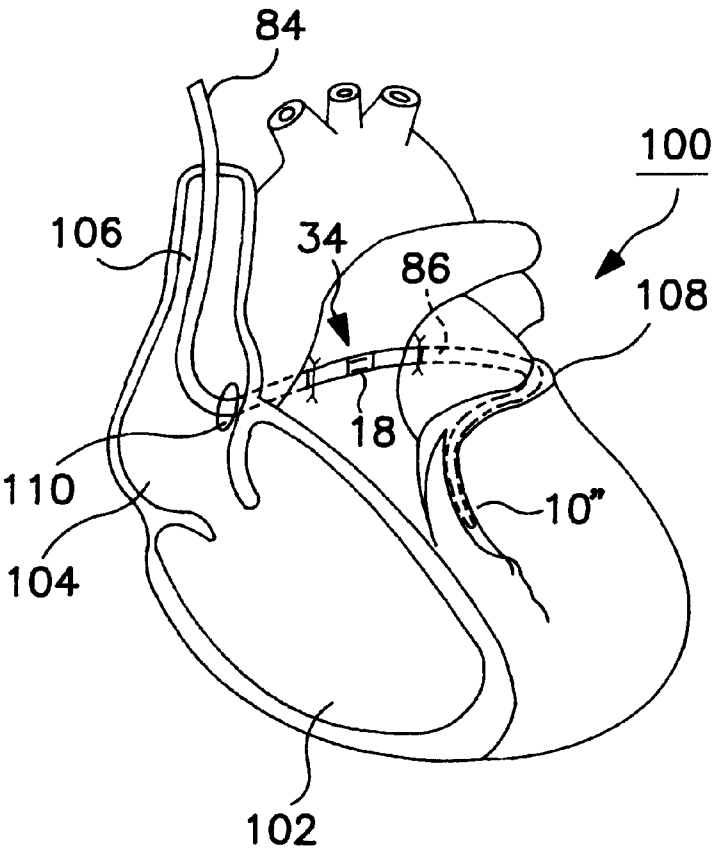
FIG. 15 is a schematic illustration of an application of the present invention in a single pass, endocardial, coronary sinus pacing lead wherein the movable electrode assembly may be positioned in the coronary sinus or in the atrium for sensing or stimulating atrial heart tissue proximally to a distal ventricular pace/sense electrode positioned deep in the coronary sinus or a tributary thereto adjacent the ventricles.

FIG. 15 is a schematic illustration of an application of the present invention in a single pass, endocardial, coronary sinus pacing lead 184 wherein the movable electrode assembly 34 may be positioned in the coronary sinus 108 or in the atrium 104 for sensing or stimulating atrial heart tissue proximally to a distal ventricular pace/sense electrode 10" positioned deep in the coronary sinus or a tributary thereto adjacent the ventricle 102. Alternatively, the movable electrode assembly 34 may be positioned to sense or stimulate nerves or the fat pad as described above.

Other applications will be apparent to those of skill in the art using a single or multiple movable electrode assemblies 34. In a ventricular endocardial lead, the movable electrode assembly(s) 34, 134 and electrode(s) 18, 118 could be positioned to be located in the right ventricle in order to sense conducted or ectopic R-waves superior to the ventricular apex, for example.

Theoretically, it may be possible to extend the length of the fixed commutator surface 48 along a length of the lead body that should be sufficient to traverse the largest atrial, atrial-SVC, or ventricular heart chamber so that the movable electrode 18 may be positioned anywhere along the length. It will also be understood that an elongated fixed commutator surface 48 may be periodically reduced in diameter and insulated to provide periodic exposed commutator surface rings along the length thereof. In such cases, the proximal and distal insulating sheaths 36 and 38 may be provided in excessively long lengths and trimmed to cover the exposed fixed commutator surface 48 or periodic commutator surface rings that are not covered by the electrode 18 and movable commutator surface 50 or 50', 50".

Although the above described endocardial leads have distal tip, screw-in electrodes 10", it will be understood that the present invention need not be used with leads having such distal tip electrodes. The distal tip may simply include an active or passive fixation mechanism for stabilizing the lead in the heart so that the variable position electrode assembly(s) 34, 134 may be maintained at the desired location(s).

Other modifications and equivalents to the preferred embodiments of the present invention will become apparent to those of skill in the art. Although the disclosed embodiments and variations relate to endocardial cardiac leads for stimulating cardiac tissue or nerves and/or sensing nerve impulses or the cardiac EGM at selected locations in heart chambers or associated vessels, it will be understood that the principles and teachings of the present invention may be applicable to other leads for sensing electrical signals from or stimulating other organs or tissue of the body. Therefore, the disclosed embodiments and variations should be considered as exemplary and not limiting as to the scope of the following claims.

I claim:

1. An elongated implantable lead having a proximal lead end and a distal lead end comprising:

an elongated lead body extending between said proximal lead end and said distal lead end;

a connector assembly located at the proximal end of said lead body;

a first electrical conductor having a proximal conductor end coupled with said connector assembly and extending through a proximal portion of said lead body to a distal conductor end;

an elongated outer lead sheath extending between said proximal and distal conductor ends for insulating said first electrical conductor through its length from body fluids and tissue;

means for providing an elongated, flexible, fixed commutator surface exposed to body fluids and tissue extending along said lead body;

means for coupling said elongated fixed commutator surface to said first electrical conductor distal to said proximal conductor end; and a movable electrode assembly fitted over said fixed commutator surface adapted to be moved proximally and distally with respect to said fixed commutator surface and said elongated outer lead sheath, said movable electrode assembly further comprising:

an exposed, movable electrode supported by said movable electrode assembly;

means for defining a movable commutator surface within said movable electrode assembly adapted to be moved with movement of said movable electrode assembly while making contact with said fixed commutator surface in a contact segment;

means for electrically connecting said exposed, movable electrode with said movable commutator surface; and means for electrically insulating said fixed commutator surface from exposure to body fluids and tissue.

2. The lead of claim 1, wherein said movable electrode is shaped in a band surface having a predetermined band width defining an electrode surface area, and further comprising:

means for selectively insulating a portion of said electrode surface area to thereby vary the exposed surface area or position of the electrode.

3. The lead of claim 2, wherein said selectively insulating means further comprises a movable, tubular insulating sheath fitted over said movable electrode assembly and adapted to be moved proximally and distally with respect to said movable electrode and fixed at a selected position to expose a selected distal or proximal segment, respectively, of said exposed, movable electrode thereby varying the exposed surface area and position of the electrode.

4. The lead of claim 2, wherein said selectively insulating means further comprises a movable, tubular insulating sheath fitted over said movable electrode assembly having a window opening formed therein and adapted to be rotated about said movable electrode and be to fixed at a selected angular orientation with respect thereto expose a selected segment of the movable electrode, thereby allowing the angular orientation of the movable electrode to be adjusted.

5. The lead of claim 1, wherein said movable electrode is shaped in a band surface having a predetermined band width defining an electrode surface area, and further comprising:

means for selectively varying said electrode exposed surface area or position.

6. The lead of claim 5, wherein said selectively varying means further comprises a movable, tubular insulating sheath fitted over said movable electrode assembly and adapted to be moved proximally and distally with respect to said movable electrode band surface and fixed at a selected position to expose a selected distal or proximal band segment, respectively, of said exposed, movable electrode thereby selectively varying said electrode surface area and position.

7. The lead of claim 5, wherein said selectively insulating means further comprises a movable, tubular insulating sheath fitted over said movable electrode assembly having a window opening formed therein and adapted to be rotated about said movable electrode and be to fixed at a selected angular orientation with respect thereto expose a selected segment of the movable electrode, thereby allowing the angular orientation of the movable electrode to be adjusted.

8. The lead of claim 1, wherein said fixed commutator surface is formed of a spiral wound conductor extending along said lead body to present a flexible conductive commutator surface.

9. The lead of claim 8, wherein said movable electrode assembly further comprises a tubular body having proximal and distal ends and a body lumen dimensioned to fit over said elongated outer lead sheath, wherein said movable commutator surface is formed as a further spiral wound conductor extending within said body lumen intermediate the proximal and distal ends thereof.

10. The lead of claim 1, wherein said movable electrode assembly further comprises a tubular body having a body lumen dimensioned to fit over said elongated outer lead sheath, and wherein said movable commutator surface is formed as a tubular, electrically conductive, surface within said body lumen.

11. The lead of claim 1, wherein said movable electrode assembly further comprises a tubular body having a body lumen dimensioned to fit over said elongated outer lead sheath and extends proximally to said connector assembly.

12. A method of adjusting the position of an electrode along the length of an elongated implantable lead having a proximal lead end and a distal lead end, the lead of the type comprising:

an elongated lead body extending between said proximal lead end and said distal lead end;

a connector assembly located at the proximal end of said lead body;

a first electrical conductor having a proximal conductor end coupled with said connector assembly and extending through a proximal portion of said lead body to a distal conductor end; and an elongated outer lead sheath extending between said proximal and distal conductor ends for insulating said first electrical conductor through its length from body fluids and tissue; the method further comprising the steps of:

providing an elongated, flexible, fixed commutator surface coupled to said first electrical conductor and extending along said lead body exposed to body fluids and tissue;

moving a movable electrode assembly fitted over said fixed commutator surface proximally and distally with respect to said fixed commutator surface, said movable electrode assembly bearing an exposed, movable electrode supported by said movable electrode assembly, a movable commutator surface within said movable electrode assembly adapted to be moved with movement of said movable electrode assembly while maintaining contact with said fixed commutator surface in a contact segment; and fixing said movable electrode assembly in the selected position and electrically insulating said fixed commutator surface from body fluids and tissue.

13. The method of claim 12, wherein said movable electrode is shaped in a band surface having a predetermined band width defining an electrode surface area, and further comprising the step of:

selectively insulating a portion of said electrode surface area to thereby vary the exposed surface area or position of the electrode.

14. The method of claim 13, wherein said selectively insulating step further comprises:

fitting a movable, tubular insulating sheath over said movable electrode assembly;

moving said tubular insulating sheath proximally or distally with respect to said movable electrode to a selected position to expose a selected distal or proximal segment, respectively, of said exposed, movable electrode thereby varying the exposed surface area and position of the electrode; and fixing said tubular insulating sheath in said selected position to electrically insulate the un-selected proximal or distal segment of said movable electrode from body fluids and tissues.

15. The method of claim 13, wherein said selectively insulating step further comprises:

fitting a movable, tubular insulating sheath over said movable electrode assembly, said tubular insulating sheath having a window opening formed therein;

moving said tubular insulating sheath with respect to said movable electrode to a selected position to expose a selected window of said exposed, movable electrode thereby varying the exposed surface area and position of the electrode; and fixing said tubular insulating sheath in said selected position to electrically insulate the un-selected proximal or distal segment of said movable electrode from body fluids and tissues.

16. The method of claim 13 wherein said moving step further comprises the step of:

rotating said tubular insulating sheath about said movable electrode to a selected angular orientation of said window opening to orient said selected window of said exposed, movable electrode to a desired anatomical feature.

17. An elongated implantable lead having a proximal lead end and a distal lead end comprising:

an elongated, tubular lead body extending between said proximal lead end and said distal lead end;

a connector assembly located at the proximal end of said lead body;

an electrical conductor having a proximal conductor end coupled with said connector assembly and extending through a proximal portion of said lead body to a distal conductor end proximal to said distal lead end;

an elongated, tubular outer lead sheath extending between said proximal and distal conductor ends for insulating said first electrical conductor through its length from body fluids and tissue having an outer lead sheath diameter;

an elongated inner lead sheath having a proximal sheath section extending within said outer lead sheath between said proximal conductor end and said distal conductor end and a distal sheath section extending from said distal conductor end to said distal end of said lead body;

a first wire conductor wound into an elongated exposed coil over said inner lead sheath and extending distally of said distal conductor end providing an elongated, flexible, fixed commutator surface of relatively constant commutator diameter extending along said lead body intermediate said proximal and distal ends thereof;

means for coupling said elongated exposed coil to said distal conductor end; and a movable, tubular electrode assembly having an outer surface and an inner surface of an inner diameter for making sliding contact with said outer diameter of said outer lead sheath and said commutator diameter when moved over it, said tubular electrode assembly adapted to be moved proximally and distally with respect to said fixed commutator surface and over said elongated outer lead sheath to a selected position, said movable electrode assembly further comprising:

an exposed electrode supported by the outer surface of said movable electrode assembly;

a second wire conductor wound into a second elongated exposed coil and positioned along said inner surface providing an elongated, flexible, movable commutator surface of relatively constant inner diameter for making contact with said fixed commutator surface in said contact segment;

means for electrically connecting said exposed electrode with said second wire conductor movable commutator surface; and means for electrically insulating said coiled fixed commutator surface except for said contact segment.

18. The lead of claim 17, wherein said movable electrode assembly further comprises a tubular body having a body lumen dimensioned to fit over said elongated outer lead sheath and extends proximally to said connector assembly.

19. The lead of claim 17, wherein said movable electrode is shaped in a band surface having a predetermined band width defining an electrode surface area, and further comprising:

means for selectively insulating a portion of said electrode surface area to thereby vary the exposed surface area or position of the electrode.

20. The lead of claim 19, wherein said selectively insulating means further comprises a movable, tubular insulating sheath fitted over said movable electrode assembly and adapted to be moved proximally and distally with respect to said movable electrode and fixed at a selected position to expose a selected distal or proximal segment, respectively, of said exposed, movable electrode thereby varying the exposed surface area and position of the electrode.

21. The lead of claim 19, wherein said selectively insulating means further comprises a movable, tubular insulating sheath fitted over said movable electrode assembly having a window opening formed therein and adapted to be rotated about said movable electrode and be to fixed at a selected angular orientation with respect thereto expose a selected segment of the movable electrode, thereby allowing the angular orientation of the movable electrode to be adjusted.

22. The lead of claim 17, wherein said movable electrode is shaped in a band surface having a predetermined band width defining an electrode surface area, and further comprising:

means for selectively varying said electrode exposed surface area or position.

23. The lead of claim 22, wherein said selectively varying means further comprises a movable, tubular insulating sheath fitted over said movable electrode assembly and adapted to be moved proximally and distally with respect to said movable electrode band surface and fixed at a selected position to expose a selected distal or proximal band segment, respectively, of said exposed, movable electrode thereby selectively varying said electrode surface area and position.

24. The lead of claim 22, wherein said selectively insulating means further comprises a movable, tubular insulating sheath fitted over said movable electrode assembly having a window opening formed therein and adapted to be rotated about said movable electrode and be to fixed at a selected angular orientation with respect thereto expose a selected segment of the movable electrode, thereby allowing the angular orientation of the movable electrode to be adjusted.

25. The lead of claim 17, wherein said fixed commutator surface is formed of a spiral wound conductor extending along said lead body to present a flexible conductive commutator surface.

26. The lead of claim 25, wherein said movable electrode assembly further comprises a tubular body having proximal and distal ends and a body lumen dimensioned to fit over said elongated outer lead sheath, wherein said movable commutator surface is formed as a further spiral wound conductor extending within said body lumen intermediate the proximal and distal ends thereof.

27. The lead of claim 17, wherein said movable electrode assembly further comprises a tubular body having a body lumen dimensioned to fit over said elongated outer lead sheath, and wherein said movable commutator surface is formed as a tubular, electrically conductive, surface within said body lumen.

* * * * *